(12) United States Patent
Jones

(10) Patent No.: US 6,720,012 B2
(45) Date of Patent: Apr. 13, 2004

(54) BORIC ACID ANALGESIC COMPOSITION AND METHOD OF TREATMENT USING THE SAME

(75) Inventor: Annie L. Jones, Detroit, MI (US)

(73) Assignee: A & L of Michigan, Inc., Detroit, MI (US)

( * ) Notice: Subject to any disclaimer, the term of this patent is extended or adjusted under 35 U.S.C. 154(b) by 27 days.

(21) Appl. No.: 10/113,863

(22) Filed: Apr. 1, 2002

(65) Prior Publication Data

US 2002/0182167 A1 Dec. 5, 2002

Related U.S. Application Data

(60) Provisional application No. 60/294,532, filed on May 30, 2001.

(51) Int. Cl.[7] ............................ A61K 33/22; A61K 9/06
(52) U.S. Cl. ........................ 424/659; 514/825; 514/937; 514/938; 514/944; 514/969
(58) Field of Search .................... 424/659; 514/825, 514/937, 938, 944, 969

(56) References Cited

U.S. PATENT DOCUMENTS 5,270,042 A  *  12/1993  Whitham ..................... 424/401
6,399,108 B1 *  6/2002   Girvan ........................ 424/659

FOREIGN PATENT DOCUMENTS

WO          01/35966      *  5/2001

OTHER PUBLICATIONS

Chemical Abstracts 116:221596 (1992).*
Derwent Abstract, accession No. 1999–288651; abstracting CN 1207299 (Feb. 1999).*
Chemical Abstracts 75:112856 (1971).*

* cited by examiner

*Primary Examiner*—John Pak
(74) *Attorney, Agent, or Firm*—Flynn, Thiel, Boutell & Tanis, P.C.

(57) ABSTRACT

An analgesic composition that can be applied topically comprises boric acid and a suitable carrier. The inventive analgesic composition can be used to provide pain relief to a person suffering from arthritis and any general pain associated with muscles or joints.

4 Claims, No Drawings

BORIC ACID ANALGESIC COMPOSITION AND METHOD OF TREATMENT USING THE SAME

This application claims the benefit of U.S. Provisional application No. 60/294,532, filed on May 30, 2001.

FIELD OF THE INVENTION

This invention relates generally to an analgesic composition which can be provided topically to provide relief from pain associated with joints and muscles.

BACKGROUND OF THE INVENTION

Analgesic compositions are agents which relieve pain by acting centrally to elevate pain threshold without disturbing consciousness or altering other sensory modalities. There are numerous analgesic compositions on the market used to provide pain relief from a wide variety of disorders. These analgesics generally are administered parenterally, orally or topically. Although parenteral and oral analgesics typically have an advantage of getting the analgesic composition quickly into the blood stream of the subject to effect rapid pain relief, they also have problems in that, with parenteral administration, there is a requirement of asepsis at administration, the risk of tissue toxicity from local irritation, the real or psychological pain factor and the difficulty of correcting an error and, with oral administration, there is a problem that oral administrations do not always give rise to sufficiently high plasma concentrations to be effective, some drugs may be absorbed unpredictably or irradically, the patient may have an absorption malfunction and some drugs cannot be administered orally to patients with gastrointestinal intolerance or who have had gastrointestinal surgery.

Due to the problems outlined above, the topical administration of an analgesic composition is desirable in some situations. Topical administration is typically employed to deliver an analgesic composition at or immediately beneath the point of application. This route of administration has problems in that generally most of the drug that is absorbed through the epidermis diffuses into the circulation system resulting in inadequate levels of the drug being delivered to the desired treatment site. This necessitates that the topical composition contain the analgesic in an undesirably large concentration in order to assure adequate delivery of the analgesic to the treatment site. This can result in the topical analgesic composition being unnecessarily expensive and difficult to ascertain the therapeutically effective amount of the analgesic composition to be used in the treatment.

As is apparent from the above discussion, there is a need for a topical analgesic composition which is a "natural" substance, inexpensive and effective in providing relief from pain associated with muscle and joint disorders.

Boric acid is generally used as a very weak germicide which is applied topically and aqueous solutions of boric acid have been employed as an eye wash, mouth wash and for irrigation of the bladder. Boric acid also has been employed as a dusting powder, when diluted with inert material, but to date, there has been no disclosure of topically applying boric acid for its analgesic properties.

SUMMARY OF THE INVENTION

It is an object of the present invention to provide an analgesic composition which can be applied topically to relieve pain associated with muscle and joint disorders.

It is a further object of the present invention to provide a method of relieving pain associated with muscle and joint disorders.

These and other objects of the present invention are achieved by providing an analgesic composition comprising boric acid and a pharmaceutically acceptable carrier. The boric acid composition can be applied topically at or above the treatment site to provide pain relief to the patient.

DETAILED DESCRIPTION OF THE INVENTION

The analgesic composition of the present invention comprises boric acid and a pharmaceutically acceptable carrier. The carriers used in the present invention are those typically used in topical compositions and can comprise hydrocarbon bases such as white petrolatum, absorption bases such as hydrophilic petrolatum, water in oil emulsion bases such as lanolin or cold cream, oil in water type emulsion bases such as a hydrophilic ointment and water-soluble bases such as polyethylene glycol ointment. In the present invention, a hydrocarbon ointment base is preferred, such as petroleum jelly. However, the base or carrier is not critical in that the only requirement is that it not interfere with the topical delivery of the boric acid to the treatment site.

In addition to the ointment base, a permeation enhancer also may be utilized with the boric acid in order to enhance the transportation of the boric acid across the skin barrier. Suitable permeation enhancers are readily determined by one of ordinary skill in the art and include alcohols such as polyethylene glycol.

The relative amounts of boric acid and ointment base used in the present invention can readily be determined by one of ordinary skill in the art depending on the site to be treated and the type of injury. A particularly preferred analgesic composition of the present invention consists of about 4 parts boric acid powder per 13 parts of pure petroleum jelly. In this particular composition, the boric acid powder is blended with the petroleum jelly until it is evenly distributed therein and the composition becomes smooth. This analgesic composition can be applied directly to the skin above painful muscles or joints two to three times a day in order to provide pain relief.

Although a particular embodiment of the present invention is disclosed above for exemplification purposes only, it would be well within the skill of the art to arrive at obvious modifications and variations of the present invention without departing from the spirit and scope thereof.

What is claimed is:

1. In a method of providing pain relief for arthritis, the improvement comprising topically applying to a subject in need of pain relief from arthritis an ointment composition containing a pharmaceutically effective amount of boric acid to skin above a treatment site.

2. The method of claim 1, wherein said ointment composition contains an ointment base selected from the group consisting of hydrocarbon bases, absorption bases, water in oil emulsion bases, oil in water emulsion bases, and water soluble bases.

3. The method of claim 2, wherein said ointment base is white petrolatum, hydrophilic petrolatum, lanolin, cold cream, a hydrophilic ointment, or polyethylene glycol ointment.

4. The method of claim 2, wherein said ointment base is petroleum jelly.

* * * * *